United States Patent [19]
Ostro et al.

[11] Patent Number: 5,811,118
[45] Date of Patent: Sep. 22, 1998

[54] METHODS OF TREATMENT USING UNILAMELLAR LIPOSOMAL ARACHIDONIC ACID METABOLITE FORMULATIONS

[75] Inventors: Marc J. Ostro, Pennington, N.J.; Andrew S. Janoff, Yardley, Pa.; Sharma R. Minchey, Monmouth Junction, N.J.

[73] Assignee: The Liposome Company, Inc., Princeton, N.J.

[21] Appl. No.: 333,975

[22] Filed: Nov. 3, 1994

Related U.S. Application Data

[63] Continuation-in-part of Ser. No. 152,852, Nov. 16, 1993, abandoned, and Ser. No. 180,089, Jan. 11, 1994, abandoned, which is a continuation-in-part of Ser. No. 147,898, Nov. 4, 1993, abandoned, which is a continuation of Ser. No. 876,200, Apr. 30, 1992, abandoned, which is a continuation-in-part of Ser. No. 697,314, May 7, 1991, abandoned, said Ser. No. 152,852, is a continuation-in-part of Ser. No. 821,648, Nov. 16, 1992, Pat. No. 5,262,168, which is a continuation of Ser. No. 195,228, May 18, 1988, Pat. No. 5,082,664, which is a continuation-in-part of Ser. No. 53,305, May 2, 1987, abandoned.

[51] Int. Cl.$^6$ .......................... A61K 9/127; A61K 9/133
[52] U.S. Cl. ............................ 424/450; 514/573
[58] Field of Search .............................. 424/450; 514/573

[56] References Cited

U.S. PATENT DOCUMENTS

| | | | |
|---|---|---|---|
| 4,493,847 | 1/1985 | Mizushima et al. | 424/317 |
| 4,684,633 | 8/1987 | Imagawa et al. | 514/78 |
| 4,820,732 | 4/1989 | Shell et al. | 514/573 |
| 4,880,635 | 11/1989 | Janoff | 424/450 |
| 4,955,878 | 9/1990 | See et al. | 604/181 |
| 5,077,056 | 12/1991 | Bally et al. | 424/450 |
| 5,082,664 | 1/1992 | Lenk | 424/450 |
| 5,262,168 | 11/1993 | Lenk | 424/450 |

FOREIGN PATENT DOCUMENTS

| | | |
|---|---|---|
| 0153858 | 4/1985 | European Pat. Off. . |
| 0 416 527 | 9/1990 | European Pat. Off. ........ A61K 9/127 |
| 0 512 916 | 11/1992 | European Pat. Off. ..... A61K 31/557 |
| 0 292 403 | 8/1994 | European Pat. Off. ..... A61K 31/557 |
| 4-356421 | 12/1992 | Japan ........................... A61K 31/557 |
| 2050287 | 1/1981 | United Kingdom . |

OTHER PUBLICATIONS

Mizushime, J. Rheumatology 14, p. 97, 1987.
Gilman, et al., ed., *Goodman and Gilmans's "The Pharacological Basis of Therapeutics"*, Eighth Edition, Pergamon Press, New York, 600–611 (1990).
Hoshi, et al., (Drug. Exptl. Clin. Res. 12(8), 681, 1986.
Jugdutt, et al., "Dissimilar Effects of Prostacyclin, Prostaglandin E1, and Prostaglandin E2 on Myocardial Infarct Size after Coronary Occlusion in Conscious Dogs", Circulation Research, vol. 49, No. 3, pp. 685–700 (1981).
Mizushima, et al., "A Multicenter Double Blind Controlled Study of Lipo–PGE$_1$, PGE1 Incorporated in Lipid Microspheres, in Peripheral Vascular Disease Secondary to Connective Tissue Disorder", J. Rheumatol. 14:97–101 (1987).
Bone, et al., "Randomized Double–Blind, Multicenter Study of Prostaglandin E1 in Patients with the Adult Respiratory Distress Syndrome", Chest, 96(1):114–119, Jul. 1989.

*Primary Examiner*—Gollamudi S. Kishore
*Attorney, Agent, or Firm*—Kenneth B. Rubin; Rosanne Goodman

[57] ABSTRACT

This invention provides a method of administering an arachidonic acid metabolite, such as prostaglandin E1, to an animal. The metabolite is given to the animal, typically a human, in association with a unilamellar liposome comprising a lipid and a release-inhibiting aqueous buffer. This method can be used to treat animals afflicted with disorders characterized by cell activation and adhesion, inflammation or toxemia.

10 Claims, 11 Drawing Sheets

*P<0.06

METHODS OF TREATMENT USING UNILAMELLAR LIPOSOMAL ARACHIDONIC ACID METABOLITE FORMULATIONS

This application is a continuation-in-part of U.S. Ser. No. 08/152,852, filed Nov. 16, 1993, now abandoned, which-in-turn is a continuation-in-part of U.S. Ser. No. 07/821,648, filed Nov. 16, 1992, now U.S. Pat. No. 5,262,168, which-in-turn is a continuation of U.S. Ser. No. 07/195,228, filed May 18, 1988, now U.S. Pat. No. 5,082,664, which-in-turn is a continuation-in-part of U.S. Ser. No. 053,305, filed May 2, 1987, now abandoned, and this application is also a continuation-in-part of U.S. Ser. No. 08/180,089, filed Jan. 11, 1994, now abandoned, which-in-turn is a continuation-in-part of U.S. Ser. No. 147,898, filed Nov. 4, 1993, now abandoned, which is a continuation of U.S. Ser. No. 07/876,200, filed Apr. 30, 1992 and now abandoned, which-in-turn is a continuation-in-part of U.S. Ser. No. 07/697,314, filed May 7, 1991 and now abandoned. The application is directed to the therapeutic uses of unilamellar liposomal arachidonic acid metabolite formulations.

The various prostaglandins are grouped into several categories (A–I), which are distinguished by varying substituents on the five-carbon ring introduced into the twenty-carbon fatty acid precursor during prostaglandin synthesis. These groups can be further subdivided based upon the number, and position, of double bonds in the prostaglandins' carbon chains. Prostaglandins are believed to act on their target cells by way of cellular surface receptors; these receptors are believed to be coupled to second messenger systems by which prostaglandin action is mediated. Prostaglandins can have a broad spectrum of biological activities.

Enzymes in the body can rapidly deactivate prostaglandins. This typically necessitates frequent administrations of high doses of the compounds to maintain therapeutically effective levels in the serum, thereby increasing the expense of prostaglandin treatment and leading to the possibility of unwanted side effects. Furthermore, as prostaglandin deactivation occurs primarily as blood passes through the lungs, the compounds are generally administered intra-arterially. Liposomal formulations can prolong the circulatory half-lives of arachidonic acid metabolites, e.g., prostaglandins, and can help avoid their deactivation in the lungs. Accordingly, such liposomal formulations can useful provide therapeutic alternatives.

Mizishuma et al. (J. Rheumatol. 14:97 (1987)) and Hoshi et al. (Drugs. Exptl. Clin. Res. 12(8):681 (1986)) describe lipid microspheres containing prostaglandin $E_1$ ($PGE_1$). However, as disclosed in Mizishuma et al. (U.S. Pat. No. 4,493,847) and Imagawa et al. (U.S. Pat. No. 4,684,633), these "microspheres" are actually prostaglandin-containing fat emulsions, which are not liposomes, and have neither the same properties, nor the same advantages, as the liposomal arachidonic acid metabolite formulations provided herein. Shell and See (U.S. Pat. Nos. 4,820,732 and 4,955,878) disclose treatments for reducing dysfunction during angioplasty procedures which involve administering prostaglandin-containing compositions to patients. These compositions also contain a carrier. However, the liquid carriers disclosed, e.g., dehydrated alcohols and saline solutions, generally cannot provide sustained release of an arachidonic acid metabolite. The fat-laden microsphere carriers disclosed are taught to be at least as large as a red blood cell, i.e, at least 7 microns in diameter, and can be much larger. Administration of particles of such large size to animals can cause difficulties because the microspheres can become stuck in, and clog, small blood vessels, e.g., lung capillaries. The liposomes used in this invention, by contrast have a maximum size of about 5 microns or less, and are preferably about 50 nm to about 1 micron in size. These liposomes can safely be administered to animals for therapeutic purposes.

Liposomal formulations of drugs can have an enhanced therapeutic index by reducing the drug's toxicity, increasing its efficacy, or both. The liposomal arachidonic acid metabolite formulations employed in the practice of this invention are useful in ameliorating or preventing diseases, disorders or conditions such as toxemic disorders, inflammatory disorders and cell activation and adhesion disorders.

SUMMARY OF THE INVENTION

This invention provides a method of administering an arachidonic acid metabolite to an animal, the method comprising administering to the animal a composition comprising a pharmaceutically acceptable carrier and a unilamellar liposome comprising the metabolite, a lipid and a release-inhibiting aqueous buffer. Preferably, the animal is a human and the administration comprises intravenous administration.

Preferably, the unilamellar liposome is a large unilamellar liposome (LUV), more preferably, an LUV having a diameter of about 100 nm. Preferably, the arachidonic acid metabolite administered to the animal is a prostaglandin, more preferably a prostaglandin of the E or I series, and most preferably, prostaglandin El. Preferably, the lipid is a saturated acyl chain lipid, more preferably, dipalmitoyl phosphatidylcholine (DPPC). Preferably, the buffer is a citric acid buffer, more preferably, a citric acid buffer having a pH of about 4.5.

The method of this invention can be used to treat animals afflicted with disorders characterized by cell activation and adhesion, inflammation or toxemia, amongst other indications, Such disorders include, without limitation: reperfusion injury, myocardial infarction, vaso-occlusive disease, adult respiratory distress syndrome (ARDS), systemic inflammatory response syndrome (SIRS), vasculitis, post-traumatic shock, burn injury, vaso-occlusive disorders, arthritic disorders, for example, gout, rheumatoid arthritis or filary attires, and autoimmune disorders, for example, systemic lupus erythematosus, juvenile diabetes, multiple sclerosis or Hashimoto's thyroiditis. Particularly preferred indications are ARDS and SIRS.

The method comprises administering to the animal an amount of the liposome which comprises an anti-disorder effective amount of the arachidonic acid metabolite. Generally, the anti-disorder effective amount of the metabolite is at least about $10^{-12}$ g of the metabolite per kg of body weight of the animal, and is typically from about $10^{-12}$ g per kg to about $10^{-3}$ g per kg. Desirably, the effective amount of the metabolite is from about $10^{-8}$ g per kg of body weight to about $10^{-4}$ g per kg. More desirably, the effective amount of the arachidonic acid metabolite is about $10^{-6}$ g per kg of body weight.

The liposome used in the method of this invention can comprise a drying protectant, and can be dehydrated, stored and then reconstituted prior to use. The drying protectant is preferably a saccharide such as maltose, lactose, sucrose, dextrose, raffinose or trehalose. Preferably, the saccharide drying protectant is maltose.

The method of this invention can comprise administering an additional bioactive agent, such as an anti-inflammatory or antimicrobial agent, to the animal.

DETAILED DESCRIPTION OF THE INVENTION

Figure 1:
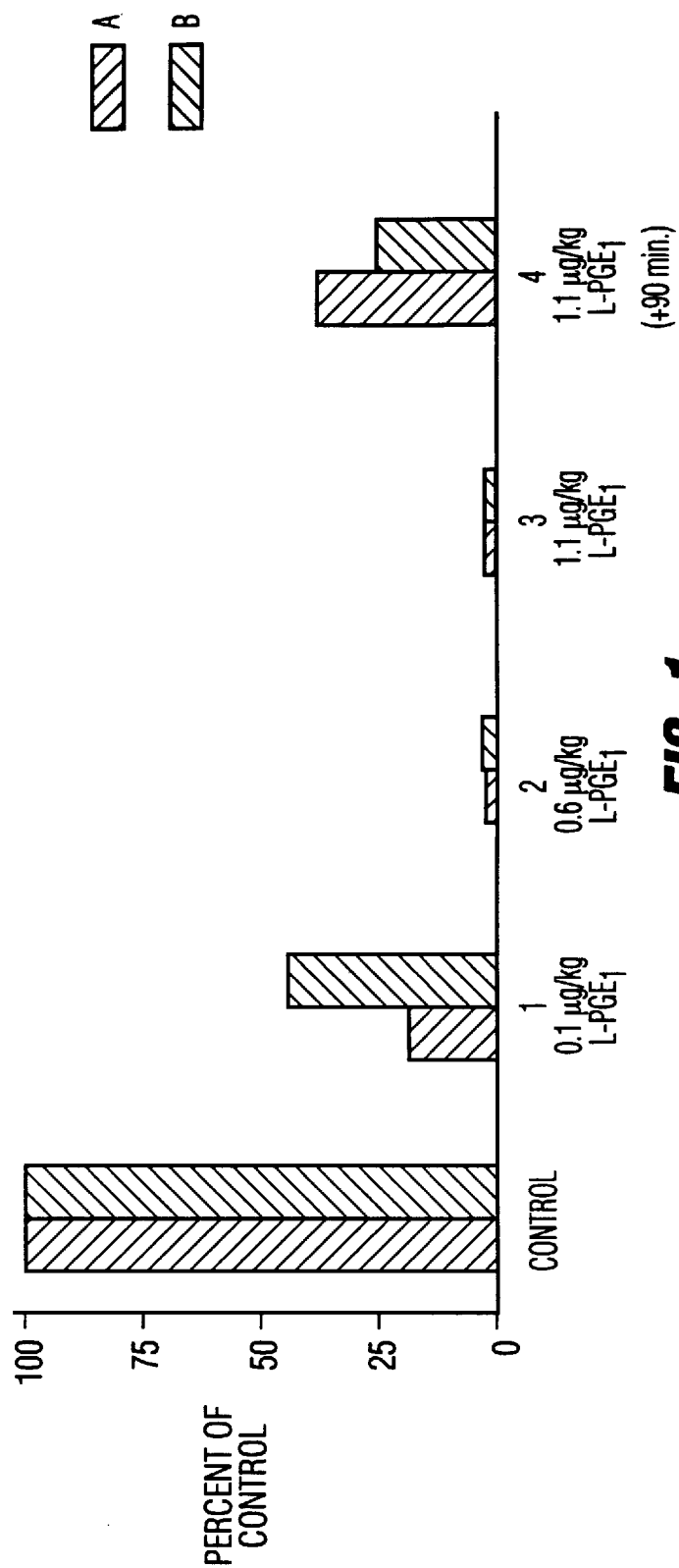
FIG. 1. Effect of LUV-PGE1 on Platelet Aggregation. LUV-PGE1 ("C-53"; prepared in accordance with the procedures set forth in Example 1, below). X-axis: control, 0.1 microgram, 0.6 microgram, 1.1 microgram and 1.1 microgram post-administration LUV-PGE1 per kg of body weight (darkly shaded: collagen; lightly shaded: U46613). Y-axis: percent of control.

This invention provides a method of administering an arachidonic acid metabolite to an animal. The method comprises administering to the animal a composition comprising a pharmaceutically acceptable carrier and the arachidonic acid metabolite in association with a unilamellar liposome. Preferably, the animal is a human and the administration comprises intravenous administration, "Pharmaceutically acceptable carrier" as used herein means any of the standard carriers, diluents, excipients and the like generally intended for use in connection with the administration of bioactive agents to animals, particularly humans. Such carriers are well known in the art and are generally chosen with regards to a number of factors, such as the particular drug being used and the intended route of administration, which are well understood by the ordinarily skilled artisan, or are within his purview to determine without undue experimentation. Suitable carriers include, but are not limited to salt solutions such as physiological saline (10 percent weight by volume sodium chloride in water), aqueous dextrose solutions, e.g., D5W (5 percent weight by volume dextrose in water), and the like. The pharmaceutical composition can further comprise auxiliary agents such as preservatives, anti-oxidants and the like in amounts, and for reasons, well known to the ordinarily skilled artisan.

Liposomes are self-assembling structures comprising one or more bilayers of amphipathic lipid molecules, each of which bilayers surrounds an aqueous compartment. Accordingly, liposomes can be unilamellar, i.e., have a single lipid bilayer, or liposomes can be multilamellar, i.e., have two or more lipid bilayers. The liposome of this invention is a unilamellar liposome. Preferably, the liposome is a large unilamellar liposome (LUV), and more preferably, is an LUV with a diameter of about 100 nm.

Liposomes can be prepared by a variety of techniques well known to ordinarily skilled artisans. For example, see Deamer and Uster, "Liposome Preparation: Methods and Mechanisms," in: *Liposomes* (M. Ostro, ed.), Marcel Dekker (New York), pp. 27–51 (1983); Cullis et al., in: *Liposomes, From Biophysics to Therapeutics* (M. J. Ostro, ed.), Marcel Dekker, pp. 39–72 (1987)). Bangham's procedure (J. Mol. Biol. 13:238 (1965)) produces "ordinary" multilamellar vesicles (MLVs), i.e., liposomes with two or more lipid bilayers, and involves dissolving one or more amphiphilic lipids in one or more organic solvents. The lipids are then dried, and the dried lipids are rehydrated with an aqueous solution so as to form the MLVs. Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having a solute entrapped in their aqueous compartments, the concentration of the solute in each of the compartments being substantially equal. Unilamellar liposomes can be formed by ether or ethanol injection or infusion methods. Unilamellar liposomes can be produced from multilamellar liposomes by extrusion of the multilamellar liposomes, under pressure, through filters with defined pore sizes according to the disclosures of Cullis et al. (U.S. Pat. No. 4,975,282) and Loughrey et al. (U.S. Pat. No. 5,059,421). Extrusion, as well as such procedures as homogenization, milling sonication and French Press application can be used to reduce liposome size, which can be determined by such procedures as freeze-fracture electron microscopic examination of the liposome, as well as quasi-elastic light scattering.

"Arachidonic acid metabolites" are prostaglandins, or compounds which can be converted to prostaglandins, e.g., artificially or in the body of an animal. Prostaglandins are a group of twenty-carbon fatty acids containing a five-carbon ring, plus seven- and eight-carbon chains, that are made from arachidonic acid and other twenty-carbon fatty acids having at least three double bonds (e.g., the "essential" fatty acids 8,11,14-eicosatrienoic acid, 5,8,11,14-eicosatetraenoic acid or 5,8,11,14,17-eicosapentanoic acid; see, e.g., *Goodman and Gilman's The Pharmacological Basis of Therapeutics*, supra). Arachidonic acid is the most abundant of these twenty-carbon prostaglandin precursors in humans.

The twenty-carbon essential fatty acid prostaglandin precursors, intermediates formed during prostaglandin synthesis, e.g., prostanoic acid, and structural analogs which can be converted to these compounds, are "arachidonic acid metabolites." "Prostaglandin-related compounds," e.g., leukotrienes, thromboxanes, lipoxins and prostacyclins, include those compounds which are functionally related to prostaglandins and which can also be derived from the twenty carbon essential fatty acid prostaglandin precursors. Prostaglandins, prostaglandin-related compounds, and eicosanoids, as well as structural analogs which can be converted to such compounds, are also "arachidonic acid metabolites." Preferably, the arachidonic acid metabolite administered to animals in accordance with the practice of this invention is a prostaglandin, more preferably, an E or I series prostaglandin, and most preferably, prostaglandin E1.

"Association" of an arachidonic acid metabolite with a liposome generally means that the metabolite is entrapped in the liposome's aqueous compartment, or is associated with the inner or outer monolayer of the liposome's bilayer, for example by way of electrostatic interactions between the metabolite and the headgroups of the monolayer's component amphipathic lipids. A preferred method for forming the unilamellar liposomal formulations of this invention is the association of the metabolite with the lipid in ethanol similar to the technique of Batzri et al., Biochim. et Biophys. Acta., 298:1015 (1973) using a transmembrane concentration gradient as disclosed in Bally et al. (U.S. Pat. No. 5,077,056). In this technique, lipid and prostaglandin are co-dissolved in an aqueous-miscible organic solvent such as ethanol, then added slowly to a first aqueous solution. Optionally, a preservative such as butylated hydroxytoluene (BHT) may be admixed with the lipid in the solution, The resulting liposome dispersion may be size-reduced to a more homogenous population, for example, by extrusion through a filter, preferably of 100 nm pore size, the filter being of either the straight path or tortuous path type. A preferred filter for use in this process is an aluminum oxide porous film such as the Anopore™ filters made by Anotec Separations. Such a population of liposomes may be formed by the extrusion procedures of U.S. Pat. No. 5,008,050. Such extrusion procedures, wherein the liposomes are passed through a filter under pressure, allow the formation of homogenous populations of liposomes with regard to size. When the liposomes are passed more than one time through the filter, the number of passes required will be determined by that necessary to achieve the desired liposome size.

The filter sizes used in the invention are chosen according to the desired size of the final liposome product. In the present invention, liposomes having an average diameter of less than about 200 nm are preferred. The individual liposome used in this invention is preferably less than about 500 nm in diameter. More preferably, the liposome has a diameter of about 100 nm, as liposomes of this size are generally known to pass through the capillary bed of the lung and are therefore able to pass through to other organs and tissues. Therefore, a filter having a pore size of about 100 nm is preferably chosen for use in the extrusion step. The size-reduced liposomes may also be sterile filtered, such as by passage through a 220 nm Millipak filter (Millipore, Inc., Bedford, Mass.).

The unilamellar liposome used in the method of this invention comprises the metabolite, a lipid and a release-inhibiting aqueous buffer. The lipid preferably increases the strength of metabolite-lipid interactions, and thereby inhibits release of the metabolite from the liposome. Such lipids are "release-inhibiting lipids." Lipid based factors which tend to increase the strength of prostaglandin-lipid interactions include, but are not limited to, those factors which tend to make lipid bilayers less permeable to water and other small molecules, e.g., those factors which tend to increase Van der Waals, dipole-dipole and other interactions between acyl chains and hence, make acyl chains pack more closely together in the bilayer. For example, the number of double bonds in the bilayer's acyl chains can affect the chains' arrangement with respect to each other in the bilayer. The lower the number of double bonds, the more closely acyl chains are likely to pack together, and hence, are more likely to present a barrier to a prostaglandin transiting the bilayer. Accordingly, preferred lipids have saturated acyl chains. The preferred lipid with saturated acyl chains is dipalmitoyl phosphatidylcholine (DPPC). However, other saturated chain lipids can also be used.

Aqueous buffers in liposomes can also inhibit or prevent release of an arachidonic acid metabolite associated with a liposome. Such aqueous buffer are "release-inhibiting aqueous buffers." Characteristics of preferred release-inhibiting buffers include, but are not limited to, the ability to establish electrostatic repulsions with the metabolites or to enhance metabolite-lipid interactions. Furthermore, buffers with a higher buffering capacity, and hence a greater ability to maintain the desired pH, will be better release-inhibiting buffers. Preferred release-inhibiting buffers are citric acid buffers, particularly those citric buffers having a pH of about 4.5.

The method of this invention can be used to administer an arachidonic acid metabolite to an animal afflicted with a disorder characterized by cell activation and adhesion, inflammation and/or toxemia, amongst other indications. The method comprises administering to the animal an amount of the liposome comprising an anti-disorder effective amount of the metabolite. Disorders treatable in accordance with the practice of this invention include, without limitation: reperfusion injury, systemic inflammatory response syndrome (SIRS), adult respiratory distress syndrome (ARDS), myocardial infarction, vasculitis, burn injury, post-traumatic shock, vaso-occlusive disorders, arthritic disorders, such as rheumatoid arthritis, gout and filary arthritis, and auto-immune disorders such as systemic lupus erythematosus, juvenile diabetes, multiple sclerosis and Hashimoto's thyroiditis.

Certain disorders are characterized by the abnormal activation of cells, e.g., platelets and neutrophils, in the blood, and by the subsequent adhesion of these cells to each other or to activated cells in the surrounding vascular endothelium. Such cell activation and adhesion disorders are a significant problem in a wide variety of medical pathologies. Endothelial cells, for example vascular, plural, pericardial or abdominal endothelial cells, can be activated by cytokines, e.g., interleukin-1 (IL-1), tumor necrosis factor-alpha (TNF-alpha) or bacterial endotoxins. In like manner, blood cells, particularly neutrophils and platelets, can be activated by agents such as GM-CSF, bacterial endotoxins, bacterial chemoattractants, TNF-alpha and the C5a component of complement.

Activated cells have adhesion sites on their surfaces by which they can adhere to each other. Activated and adhered cells can form clumps, which can clog small blood vessels such as those found in the lungs and heart, and thereby reduce blood flow to surrounding tissue. The activated cells can also adhere to activated vascular endothelial cells; such adhesion can lead to subsequent degranulation of vascular endothelium, or to the release of mediators of cell damage, such as superoxide anion ($O_2^-$) and proteolytic enzymes.

Amongst the cell activation and adhesion disorders to which the present invention is directed are reperfusion disorders, such as those related to the reperfusion of occluded blood vessels, or incidental to surgery in which blood flow is temporarily stopped (see, e.g., Seewaldt-Becker et al., "Effect of Anti-Adhesive Antibodies on Reperfusion Injury," (Springer et al., eds.) in: *Leukocyte Adhesion Molecules,* Springer-Verlag, New York (1990) pp. 138–148; and "Adhesion in Disease and Therapy," (Springer et al., eds.), in: *Leukocyte Adhesion Molecules,* Springer-Verlag, New York (1990), pp. 85–156). When there is a blockage in a blood vessel, surrounding endothelial cells, as well as downstream ischemic tissue, can be damaged. There can even be further damage to nearby endothelial cells when the occlusion is cleared. Such damaged cells can in turn induce activation in neutrophils and platelets after restoration of blood flow to the affected areas.

The same cells which become activated and subsequently undergo intracellular adhesion can also have surface receptors for arachidonic acid metabolites. Without intending to be limited by theory, it is believed that treatment with arachidonic acid metabolites, by binding to these receptors, can reduce cell activation and adhesion disorder-associated damage by deactivating the cell surface receptors responsible for the elevated levels of intercellular adhesion.

$PGE_1$ and $PGI_2$ have been found (see, Jugdutt et al., "Dissimilacts of Prostacycn, Prostaglandin E Prostaglandin Myocardial Infarct ze after Coronarusion in Conscious," Circulation CH, 49(3):685–700 981) to have scant effect in reducing the infarct size in dogs which were reperfused after simulation of a myocardial infarction by placement of an occluder snare around a coronary artery. In the reported tests, the prostaglandin was administered via continuous arterial infusion over a six-hour period, resulting in the administration of a relatively large dose of the drug. The need for this continuous infusion is believed to be that free, i.e., non-liposomal, prostaglandins such as $PGE_1$ have an extremely short half life in vivo, and have to be continuously replenished to maintain an effective blood level. Furthermore, it is believed that the prostaglandin is rapidly inactivated when the blood passes through the lungs, which necessitates arterial infusion rather than a simpler intravenous administration. Additionally, the distribution of high levels of $PGE_1$ in vivo is known to induce systemic effects such as hypotension, tachycardia and diarrhea.

When patients are subject to the insults that can lead to ARDS, such as, to trauma, burns, sepsis, aspiration and hyperoxia, many organs in the body other than the lungs can be affected. The causes and clinical courses of this condition can vary widely. For example, in the case of a patient with a severe infection endotoxin is released from the bacterial cell walls, and the inflammatory cascade is initiated, leading to septic shock. Again, as sepsis/trauma syndrome is not limited in causation to infections it is possible that no endotoxin is involved, but nonetheless, the release of factors such as TNF, IL-1 complement and leukotrienes is triggered.

Angioplasty is a technique whereby a balloon is inserted into an occluded artery and inflated in order to open blocked blood vessels. Although this technique has become quite routine in the management of coronary artery disease in the six month period following this procedure, over 33% of the treated patients experience restenosis, or reocclusion of the previously opened blood vessel. It is thought that this condition starts with injury to the vascular endothelium which often results form the balloon procedure. The exposed extracellular matrix will rapidly bind to several layers of activated platelets. Once platelets bind, they will release a variety of growth factors which will result in the proliferation of smooth muscle cells underlying the vessel to the point where the vessel becomes reoccluded. By preventing platelets from binding to the extracellular matrix, one can disrupt the cascade of events resulting in restenosis. Thus, acute administration at the time of the angioplasty procedure of a drug that prevents platelet adhesion could prevent restenosis.

Recently, De Servi et al., European Heart Journal, "Prostaglandin E administration in unstable angina patients undergoing PTCA; preliminary results", August 1990, published the results of a clinical trial in patients with unstable angina who were given an intracoronary infusion of $PGE_1$ prior to and following angioplasty. The drug was infused over a 24-hour period. The results of this study showed that the rate of restenosis six months after angioplasty in the $PGE_1$-treated group was reduced by almost 50% verses the untreated control group, even though the treatment with $PGE_1$ only lasted 24 hours.

Acute myocardial infarction (more commonly referred to as a heart attack) refers to a blockage of the blood supply to the muscles of the heart, usually caused by a blood clot. If the blood is prevented from reaching the heart for too long, the patient will die. When an occlusion of the coronary artery occurs, the patient is either treated with a fibrinolytic agent, such as tissue plasminogen activator (tPA) or streptokinase, to dissolve the clot, or the blockage may resolve itself. In both instances, blood flow is resumed to the ischemic (oxygen-deprived) region of the heart. This reflow of blood into the heart is called reperfusion. While reperfusion is necessary to save the patient's life, it causes further injury to the heart muscle called reperfusion injury. Reperfusion injury is known to be the end result of the inflammatory cascade.

In addition to the problem of reperfusion injury following clot removal, patients suffering from a myocardial infarction may suffer from other secondary problems. For example, after the normal blood flow is restored to the heart, both neutrophils and platelets are activated. Activated platelets often adhere to one another and begin to reocclude the coronary artery, resulting in a situation where the rate of blood flowing to the heart decreases over time. In some cases, complete reocclusion will occur. $PGE_1$, in addition to preventing neutrophil binding to endothelial cells, prevents platelet aggregation and reduces, if not eliminates, the no reflow phenomenon.

Sharma et al,, The American Journal of Cardiology, "Intracoronary Prostaglandin $E_1$ Plus Streptokinase in Acute Myocardial Infarction", page 1161, December 1986, vol. 58, has shown in a clinical setting of acute myocardial infarction that administration of free $PGE_1$ by slow intracoronary infusion together with intracoronary streptokinase provides positive clinical results when compared with a control group taking intracoronary streptokinase alone. The results showed decreased time to reperfusion, reduced dose of streptokinase required, increased percentage of vessels patent after 10 days, and higher ejection fractions. Drawbacks of the study are that the drug must be given by slow intracoronary infusion which is cumbersome and requires specialized facilities and highly trained personnel. Also this approach requires careful titration of the dose of $PGE_1$ so that significant drops in blood pressure can be seen.

Inflammation is a process of cytological and histological reactions occurring in affected blood vessels, and surrounding tissues, in response to an injury (see, e.g., *Stedman's Medical Dictionary (Illustrated)* (24th edition, J. V. Basmajian et al., eds.), Williams and Wilkins, Baltimore, Md. (1982), pp. 707–708). Inflammatory responses to such stimuli include local reactions and resulting morphological changes, destruction or removal of injurious materials and activation of repair mechanisms. Thus, inflammation can be part of the process by which animals heal themselves.

However, inflammation can also occur in response to abnormal physiological stimuli and can cause problems in the body. Joints, for example, become inflamed in arthritic conditions such as gout, filary arthritis, rheumatoid arthritis and Lyme disease (see, e.g., *Stedman's Medical Dictionary (Illustrated)*, supra at pages 123–124). These states may be characterized by the extravasation of cells, i.e, the egress of cells from the circulation into the inflamed area. Agents, such as prostaglandins, which can inhibit such extravasation, or which can otherwise inhibit inflammatory responses to abnormal physiological stimuli, can be used to ameliorate the inflammation.

Toxemia is the clinical manifestations observed during the course of infections by infectious agents, e.g., microbes which contain toxins and other substances poisonous to host animals. For example, during infections by certain gram-negative bacteria such as *E. coli*, a lipopolysaccharide (LPS) is released from the cell wall as it is broken down. The LPS can then induce the death of cells in the host animal. Toxemic conditions occur in animals in which toxins such as LPS are made available, i.e., in septic conditions, or conditions of systemic disease caused by the multiplication of microorganisms in the circulation (see, e.g., *Stedman's Medical Dictionary (Illustrated)*, supra at pages 1274–1275 and 1464). Toxemia can also result from exposure of the animal to traumatic stimuli, e.g., physical or chemical trauma.

"Auto-immune disorders," such as systemic lupus erythematosus, juvenile diabetes, multiple sclerosis and Hashimoto's thyroiditis, are characterized by an animal's immune system attacking its own tissues.

"Anti-disorder effective" amounts of an arachidonic acid metabolite are any amounts effective to ameliorate, inhibit or prevent the cell activation and adhesion, inflammation, toxemia, or other indication associated with the disorder being treated according to the method of this invention. Typically, the effective amount of the metabolite comprises at least about $10^{-12}$ g of the metabolite per kg of body weight of the animal, and desirably, from about $10^{-12}$ g per kg to about $10^{-3}$ g/kg. More desirably, the effective amount of the metabolite comprises from about $10^{-8}$ g per kg of body weight to about $10^{-4}$ g per kg. Most desirably, the effective amount comprises about $10^{-6}$ g of the arachidonic acid metabolite per kg of body weight of the animal.

Generally, a significantly lower dosage of the liposomal metabolite, in comparison to a dosage of the free metabolite, is required to obtain the desired effect. As discussed above, because of the rapid metabolism of free prostaglandins in vivo, long continuous infusions of relatively large doses of these drugs have been required to maintain an effective blood level in the patient being treated. However, the hypotension, tachycardia and diarrhea caused by high blood levels of prostaglandins limit the amounts of free prostaglandins which can be administered. Furthermore, the high cost of prostaglandins makes it prohibitively expensive to administer such large dosages. The method of the present invention provides for the effective administration of the arachidonic acid metabolites at reduced cost and with reduced side effects.

Arachidonic acid metabolite, e.g., prostaglandin, treatment can reduce the damage exhibited in those animals afflicted with disorders characterized by cell activation and adhesion, toxemia, inflammation and other indications. The same cells which have receptors for cellular activating agents can also have surface receptors for the metabolites. It is believed that when metabolites bind to their receptors, they can deactivate the surface receptors responsible for the elevated levels of intercellular adhesion. The mechanism for this deactivation is believed to be a protein kinase A-mediated increase in intracellular cAMP levels instigated by metabolite/receptor interaction. Without cell-cell binding, cofactors such as $O_2^-$ and various degradative enzymes cannot be released, and tissue damage is eliminated.

$PGE_1$ has been shown to be a potent inhibitor of both neutrophil and platelet aggregation, as well as the binding of these cells to activated vascular endothelial cells. Arachidonic acid metabolites such as $PGE_1$ are also believed to have the ability to both prevent inflammation, and to turn it off once it has been initiated. It has been found that the extracellular release by neutrophils of mediators of inflammation can be modulated by the elevation or depletion of intracellular stores of cyclic adenosine monophosphate (cAMP).

It has been found that the extracellular release by neutrophils of mediators of inflammation can be modulated by the elevation or depletion of intracellular stores of cyclic adenosine monophosphate (cAMP) and cyclic guanosine monophosphate (cGMP). Elevation of cAMP reduces release of mediators of inflammation whereas increases in the levels of cGMP enhances the excretion of those mediators. cAMP is sometimes referred to as the "universal off-switch" since increasing intracellular levels of cAMP can turn off inflammation, regardless of the factor that initially turned it on. Importantly, some prostaglandins such as $PGE_1$ elevate cAMP, thus providing the rationale for using $PGE_1$ as an anti-inflammatory agent. $PGE_1$ can be thought of as an agent that can activate the "universal switch off". It has now been shown in vitro that $PGE_1$ inhibits the binding of neutrophils and platelets to themselves, as well as to endothelial cells, by preventing the activation of the receptors necessary to mediate cell-cell adhesion. This inhibition is coincident with the elevation of intracellular cAMP. Without cell-cell binding, cofactors such as $O_2^-$ and various degradative enzymes cannot be released, and tissue damage is eliminated. Therefore, $PGE_1$ actually acts as a potent anti-inflammatory agent. It can both prevent inflammation and turn it off, regardless of whether the mediating factor is IL-1, TNF, complement, leukotrienes or others.

Liposomes can be particularly advantageous vehicles for delivering prostaglandins to their intended sites of action. Without being bound by a particular theory or mechanism, it is believed that the liposomes are attracted to the activated cells and adhere to the activated surfaces. The prostaglandin is then readily available at the site of injury to deliver its anticellular adhesion action, One theory for the attraction of liposomes to adhesion activated cells is that liposomes are opsonized by fibronectin and vitronectin in the blood. Opsonization is the process by which bacteria are altered such that they become more readily and efficiently engulfed by phagocytes. Thus opsonized liposomes would be more readily attracted to the activated neutrophils which express receptors for fibronectin and vitronectin, thereby delivering the associated prostaglandin to the affected sites.

Liposomal arachidonic acid metabolite formulations in which the metabolite is associated with the liposome by way of a pH gradient across the liposome's lipid bilayer can be therapeutically useful. Liposomal formulations having an internal acidic aqueous buffer, such as a citric acid buffer, particularly a pH 4.5 citric acid buffer, are preferred for establishing transbilayer pH gradients. Arachidonic acid metabolites associated with liposomes by such gradients tend to remain associated with the liposome as long as the pH gradient is maintained. However, when the gradient decays in the bodies of animals to which the liposome has been administered, and the internal pH consequently increases, arachidonic acid metabolites generally become unassociated with the liposome. The metabolite then is more likely, than when it is associated with a liposome, to be able to interact with the corresponding surface receptors on cells, such as neutrophils, that become activated and that subsequently undergo intercellular adhesion.

Unilamellar liposomes used in accordance with the practice of this invention can comprise a drying protectant, which is generally a hydrophilic compound, such as a saccharide, urea, dextran, albumin or polyvinyl alcohol, capable of preventing the rearrangement of the lipids in the liposomes, so that when the liposomes are reconstituted subsequent to dehydration, a substantial portion of the contents originally entrapped in the liposomes remain therein. Drying protectants are generally strong hydrogen bond acceptors, and typically possess stereochemical features favorable to preserving the intramolecular spacing of the bilayer constituents. Saccharides, such as mannose, galactose, trehalose, raffinose, maltose, sucrose, lactose or dextrose are preferred drying protectants. Maltose is particularly preferred.

Saccharides are typically used as drying protectants at concentration of from about 5 to about 20 percent, preferably at about 10 percent, by weight of the aqueous phase used to prepare liposomes. Mannitol may be used in conjunction with any of the saccharides, but it has surprisingly been found that when used alone, mannitol does not succeed in maintaining liposome size. Mannitol may be used in concert with the saccharides in about a 0–2% concentration, preferably a 1% concentration. The total concentration of saccharide used ranges from about 5% to about 20%, preferably 10% to 12%, most preferably about 10%. Additional preservatives such as BHT or EDTA in the formulations at, for example, 5 mg BHT per ml of ethanol, and, for example, 0.01% EDTA in 10% dextrose may also be included.

Liposomal dehydration enables liposomes to be stored for extended periods of time; they can then be reconstituted on an as-needed basis for administration to subjects. Dehydration is preferably carried out using a drying protectant in connection with the liposomes, in accordance with the procedures of Schneider et al. (U.S. Pat. No. 4,229,360) and Janoff et al., (U.S. Pat. No. 4,880,635); the contents of which are incorporated herein by reference). Alternatively, the drying protectant can be omitted if the dehydration is conducted without prior freezing and sufficient water is left remaining in the liposomal preparation to maintain the integrity of a substantial portion of the liposomal bilayers through the dehydration-rehydration process.

Lyophilized prostaglandin-liposome formulations can be stable for at least one year when stored at 6 deg. C. or 25 deg. C. Insertion of the arachidonic acid metabolite into the liposome membrane, followed by lyophilization, is believed to shield the metabolite from water, and to thereby inhibit hydrolysis. Stability studies using high pressure liquid chromatography (HPLC) analysis of the formulation have shown that after storage at 6 deg. C. for one year, no degradation products of $PGE_1$ were present. When the lyophilized liposomes are to be used, rehydration is accomplished by adding an aqueous solution, e.g., distilled water, water for injection (WFI), or buffer or aqueous solution of appropriate pH, as described above, to the liposomes. The liposomes can be then resuspended into the aqueous solution by gentle mixing. The rehydration can be performed at about 25 deg. C.

The method of this invention can comprise administering an additional bioactive agent to the animal, i.e., a bioactive agent in addition to the arachidonic acid metabolite with which the liposome is associated. "Bioactive agent" as used herein denotes any compound or composition of matter which can be administered to animals. These include agents having biological activity in the animals, as well as those useful for imaging or other forms of diagnosis. Bioactive agents include, but are not limited to: antiviral, antibacterial, antifungal, antiparasitic, antimetabolic, antiglaucomic, anti-inflammatory or antineoplastic compounds, sterols, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, bronchodilators, local anesthetics, growth promoting agents, regenerative agents and the like. Additional bioactive agents are selected for particular indications according to criteria, for example, the need to treat other conditions afflicting the animal, well known to ordinarily skilled artisans given the teachings of this invention. The additional bioactive agent can be an additional arachidonic acid metabolite.

This invention is more fully described in the following Examples. However, those of ordinary skill in the art will readily understand that these examples are merely illustrative of the invention as described in the claims which follow thereafter.

| Ingredient | Per 1500 ml | Per ml |
|---|---|---|
| Egg phosphatidylcholine (EPC) | 7.06 g | 4.4 mg |
| Maltose monohydrate | 150.0 g | 100 mg |
| Ethanol (anhydrous) | 8.38 ml | 0.00558 ml |
| Butylated hydroxytoluene (BHT) | 45 mg | 0.03 mg |
| $PGE_1$ 15 mg | 0.01 mg | |
| Water for injection, USP | qs 1500 ml | |

EXAMPLES

Example 1

Liposome Preparation

A 1500 ml batch of liposomal $PGE_1$ was made up of the following components:

Preparation 1350 ml of water for injection was added to a beaker and set with a nitrogen sparge for at least 30 minutes. The 150 g of maltose (J. T. Baker, Phillipsburg N.J.) was added to the water and mixed until dissolved, with the nitrogen sparge continued. This produced 1440 ml of mixture at a pH of 4.81.

In another beaker, the 7.06 g of egg phosphatidylcholine (EPC) (Nippon Oil and Fats, Hyogo, Japan) were combined with 6 ml of ethanol (anhydrous) and mixed until dissolved, and the 45 mg of BHT was added and mixed until dissolved. To this mixture, the 15 mg of $PGE_1$ was added and mixed until dissolved, the remaining 2.37 ml of ethanol being used to rinse any remaining $PGE_1$ in the weighing container into the mixture.

The ethanol solution was drawn into a 10 ml capacity glass syringe and injected through a 14 gauge cannula slowly over a period of 11 minutes into the maltose solution with rapid mixing and continued nitrogen sparge. Upon addition of the ethanol/lipid mixture, the solution became cloudy, indicative of the formation of liposomes. The suspension was then diluted to a final volume of 1500 ml with the remaining water for injection.

The liposome dispersion was then extruded 3 times through a 0.2 um pore size Nucleopore® polycarbonate straight through path type filter (Nuclepore, Pleasanton Calif.), followed by 5 extrusions through a corresponding 0.1 μm filter The particle size of the resulting liposomes was determined to be 0.169 um (S.D. 0.041 μm), using quasi-elastic light scattering (QELS) (Nicomp Particle Sizer). The sized liposome dispersion was then passed through a 0.22 μm Millipak sterilization filter. Finally, 10.5 ml aliquots of the dispersion were filled into vials and lyophilized according to the procedures set forth as Example 2 to form a lyophilized product, which can be used immediately or stored for future use.

The lyophilized product was rehydrated with 10 ml of 0.01M acetate buffer (pH 4.3), with the resultant suspension having pH of about 4.3. Entrapment of the $PGE_1$ in the liposomes was determined by HPLC, and it was found that at least 98 percent of the available $PGE_1$ was entrapped in the liposomes, at a concentration of about 9.0 micrograms of $PGE_1$ per ml of rehydrated suspension.

Lyophilization Process

Split-top, butyl-rubber stoppered, Flint lyophilization vials of 50 ml capacity were filled with 10.5 ml of aqueous-suspended liposomes, containing $PGE_1$. These vials were placed on shelves in the lyophilizer (PV-24 Stokes Lyophilizer). The vials were held at 0 deg. C. for 1.5 hours. The shelf temperature was then decreased to minus, 45 deg. C. at a rate of 0.8 deg. C. per minute, and held for 1 hour, after which a vacuum of 100 μm Hg was applied. The shelf temperature was then increased to minus, 28 deg. C. at a rate of 0.5 deg. C. per minute, while continuing the vacuum at 100 μm Hg.

The vials were held at minus, 28 deg. C. for 50 hours at 100 μm Hg vacuum. The shelf temperature was then increased to 25 deg. C. at a rate of 0.5 deg. C./min and held for 22 hours. The vials were then stoppered under partial vacuum.

Acute Myocardial Infarction/In Vivo Test of Liposomal $PGE_1$

The rehydrated liposomes of Example 1 were tested in vivo as a means of reducing reperfusion injury incidental to the treatment of myocardial infarction resulting from occluded blood vessels. A total of 53 conditioned 25–35 kg dogs were studied in the dose-ranging trials and the infarction study. Dogs were excluded from analysis for the following reasons: extensive collateralization to the infarct zone (4), heart worms at necropsy (1) and cardiac arrest during occlusion (1). Forty dogs survived of which 27 were suitable for analysis; 7 dogs each in the control, liposomal $PGE_1$ (LUV-$PGE_1$) and liposome-control (empty, or "plain", liposomes) groups and 6 dogs in the $PGE_1$-control (free PGEL) group.

First, dose-ranging trials were conducted to determine a suitable dosage for use in the myocardial infarction studies. Incremental doses of liposomal $PGE_1$ were given while heart rate, mean arterial pressure, cardiac output and pulmonary capillary wedge pressure were measured. Blood samples were also taken at intervals for platelet aggregation studies (FIG. 1). Doses greater than 2.0 pg/kg delivered as a bolus over 10 to 20 minutes produced a marked tachycardia and transient hypotension with a significant increase (doubling) in cardiac output. Platelet aggregation was partially inhibited at 0.1 μg/kg and totally inhibited at 0.6 μg/kg. A dose of 0.5 μg/kg delivered over 10 minutes seemed to increase the heart rate and cardiac output only slightly. In order to optimize the potential results, it was elected to give two doses of liposomal $PGE_1$ of 0.5 μg/kg each. One injection was administered just after occlusion of the infarct-related artery and the other just prior to reperfusion. This regimen should insure an effect throughout the period of ischemia and initial period of reperfusion. The effect of the liposomal $PGE_1$ appeared to persist for some time after administration, This observation is significant to reocclusion after reperfusion and restenosis following angioplasty which are directly related to platelet aggregation and adherence to endothelial cells and extracellular matrix.

Figure 2:
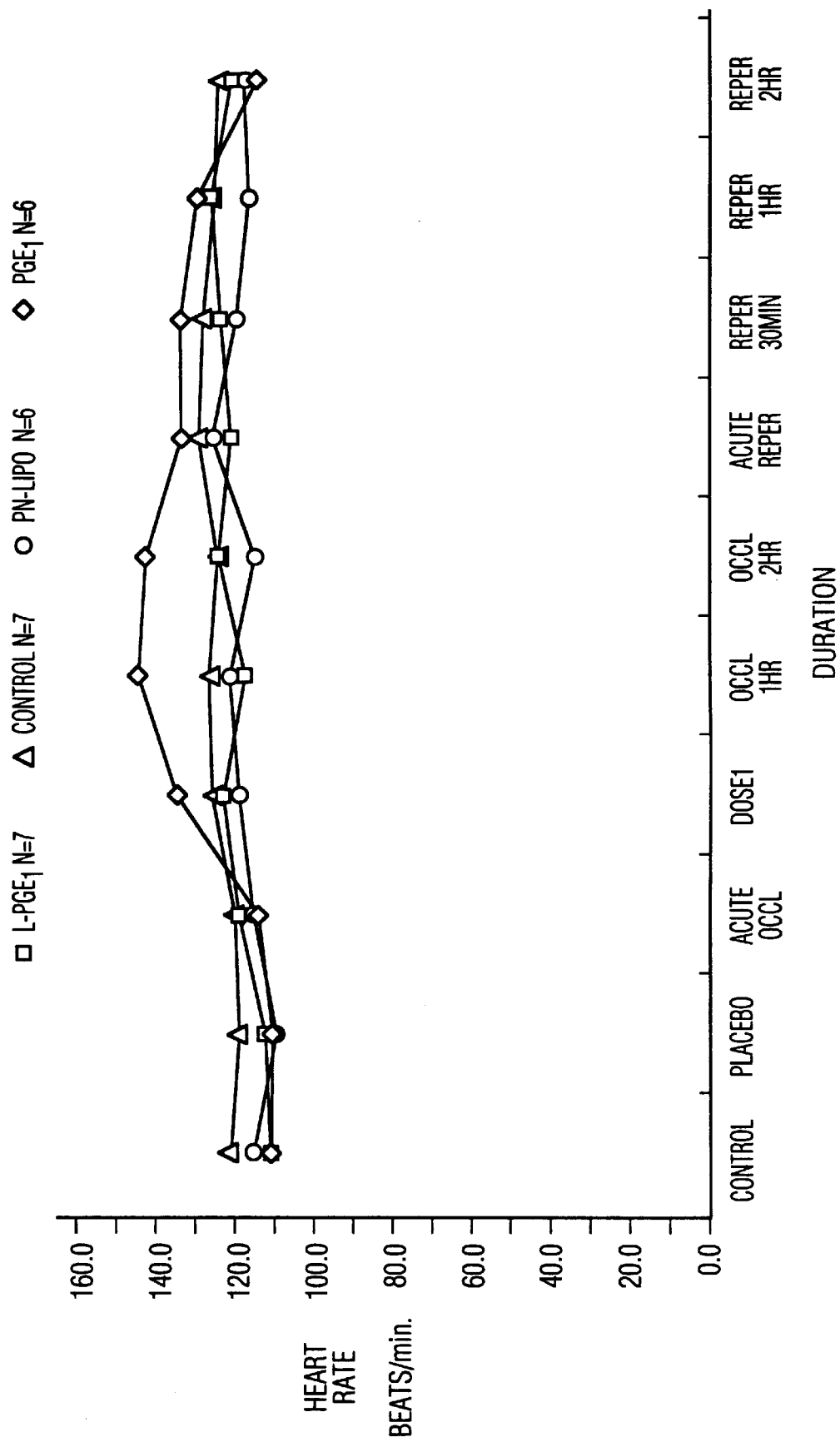
FIG. 2. Heart Rate vs. Experiment Duration in Treated/Control Dogs. Filled squares: LUV-PGE1; filled triangles: control; *: empty liposomes; filled diamonds: free PGE1.

The effects of liposomal $PGE_1$, free $PGE_1$, empty liposomes and a control group on heart rate were studied. The test dogs were anesthetized with sodium pentobarbital and maintained with intravenous pentobarbital and Inovar® (droperidol/fentanyl). Arterial occlusion was simulated by ligating the left descending aorta artery. Ten minutes after occlusion, 0.5 μg/kg liposome-bound $PGE_1$ was administered intravenously over ten minutes into a first group of dogs, with a second group of control animals maintained without treatment, The liposome infusion tended to cause an increase in heart rate which was counteracted, in part, by administration of small amounts of additional Inovar. Tests showed no major differences in heart rate throughout the experiment between the control and treated animals. One hundred minutes after occlusion, a second dose of 0.5 μg/kg was administered over ten minutes. After 2 hours, the ligature was removed, causing an acute reperfusion of the blood vessel. Two hours later, the dog was euthanized, and the heart examined for myocardial infarction damage. The results are summarized in FIG. 2. The group receiving free $PGE_1$ exhibited a significant rise in heart rate after the initial dosage and continuing until reperfusion. This rise was not noted in any of the remaining 3 groups of animals. This rise has been attributed to compensatory tachycardia due to vasodilation.

Figure 3:
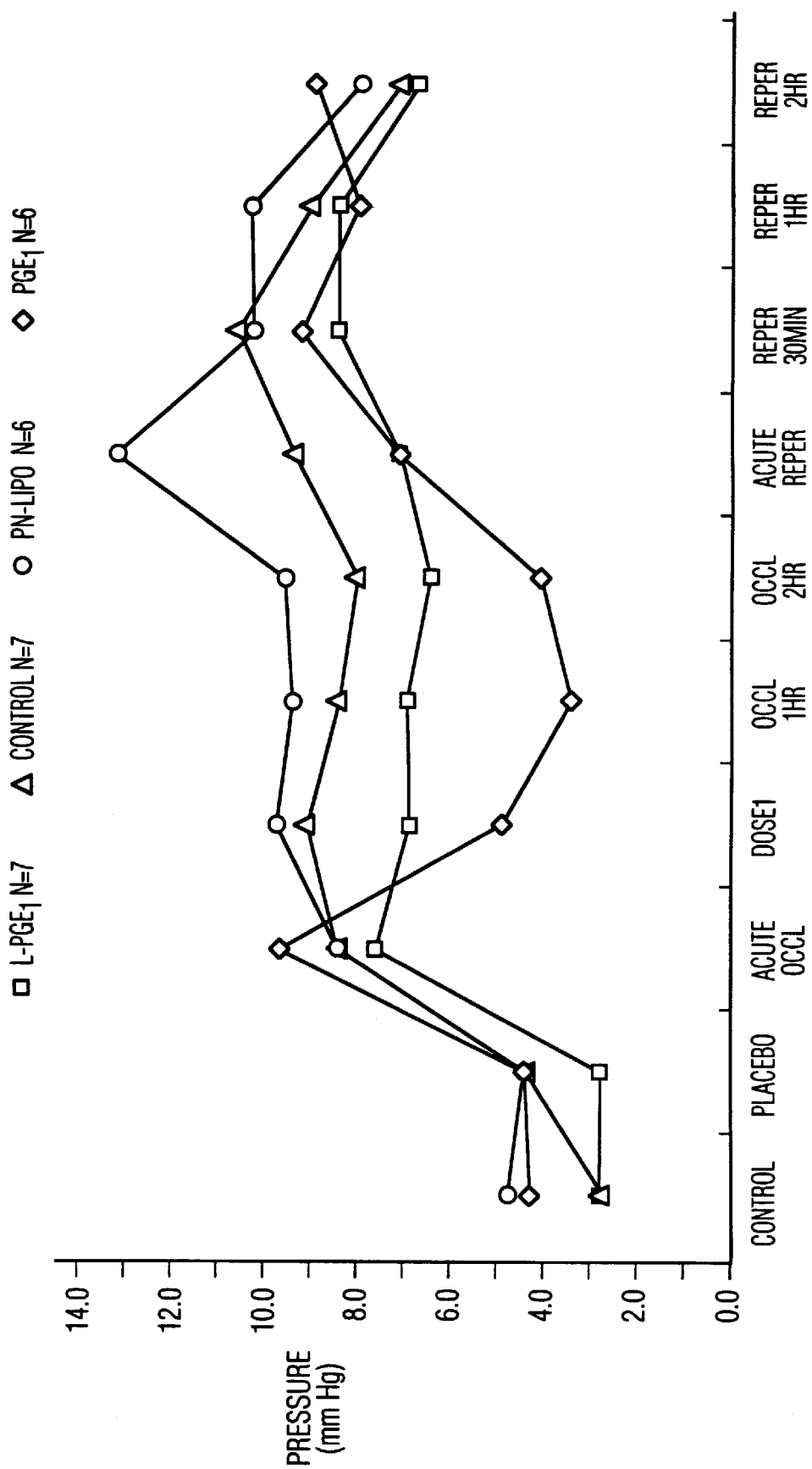
FIG. 3. Left Atrial Pressure vs. Experimental Duration. Filled squares: LUV-PGE1; filled triangles: control; *: empty liposomes; filled diamonds: free PGE1.

A total of seven dogs were included in the control group, and seven dogs were treated with liposomal $PGE_1$. During the test period, mean aortic pressure remained relatively constant, and there was no significant difference between the control and treated groups. Mean left arterial pressure increased in each group after occlusion, but there were no significant differences between the groups. Results are summarized in FIG. 3.

As anticipated, myocardial blood flow, as measured by 15 um radioactive microspheres, demonstrated a significant decrease in all groups of animals after occlusion. There was no significant improvement in collateral blood flow after liposomal $PGE_1$ infusion in the test animals suggesting that the microvascular vasodilatory effects of liposomal $PGE_1$ were minimal.

With reperfusion blood flow increased significantly higher in treated dogs compared to control animals. Examination of the hearts showed that the myocardial infarct size, expressed as a percent of region at risk (i.e. area of low flow during ischemia), appeared reduced by about 50% in the dogs treated with liposomal $PGE_1$, as compared to the untreated control dogs. In addition, the administration of liposomal $PGE_1$ resulted in an almost total inhibition of platelet aggregation in the blood.

Figure 4:
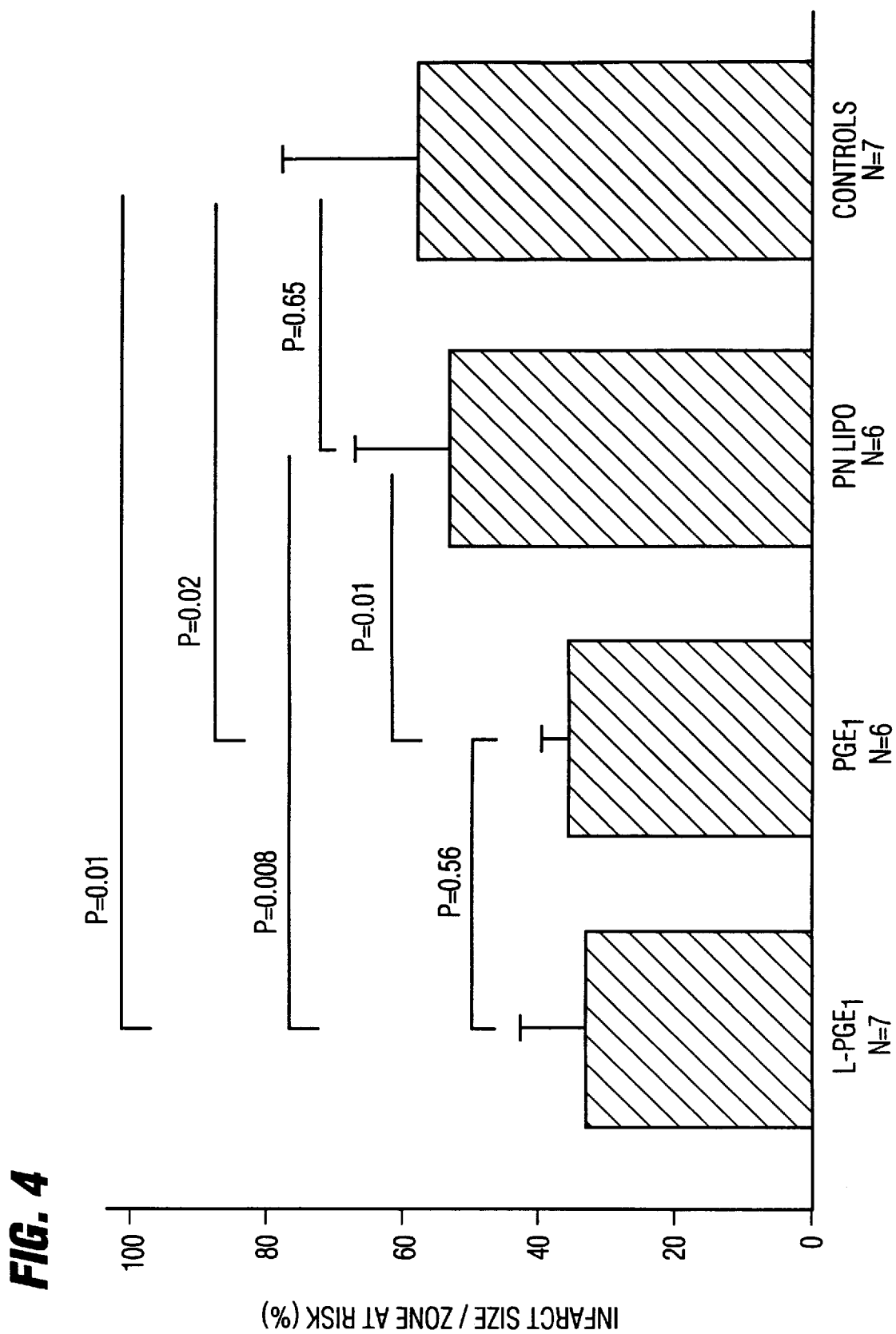
FIG. 4. Infarct Size as Percent of Zone at Risk. X-axis: LUV-PGE1, free PGE1, empty liposomes, control. Y-axis: infarct size/zone at risk (%).

FIG. 4 summarizes the results on the four groups of dogs receiving either liposomal $PGE_1$, free $PGE_1$, empty liposomes or saline control. The liposomal $PGE_1$ was given in two 0.5 µg/kg infusions over 10 minutes each for a total dosage of 1.0 µg/kg. Free $PGE_1$ was continuously infused over 90 minutes at 0.1 µg/kg/minute or at a total dosage of 9 µg/kg.

Tests were also conducted to measure the white blood cell infiltration into the ischemic tissue of the heart. Immediately following extraction of the heart from the animals, samples were obtained from the 1) infarct zone, 2) border zone of the infarct zone within the risk region, 3) risk (ischemic) zone, and 4) control zone outside the region at risk. (The region at risk was the portion of the heart supplied by the occluded blood vessel.) The tissue was flash frozen using liquid nitrogen, and kept at minus, 70 deg. C. until analyzed. Myeloperoxidase (an enzyme found only in neutrophils) activity was subsequently analyzed for each of the four zones in each animal heart. Initially, six control animals were tested in this manner, although one of these (CONT 4 in the table) was considered aberrant throughout the test, but was included in the tabulation for completeness. Only four of the animals treated with liposomal $PGE_1$ (LIPO 1–4) were included in this portion of the study. The results are presented in tabular form in Table 1, with the level of myeloperoxidase expressed in arbitrary units of enzyme for comparative purposes:

TABLE 1

MYELOPEROXIDASE RELEASED FROM MYOCARDIAL TISSUES

| DOG | ZONE | | | |
|---|---|---|---|---|
| | 1 | 2 | 3 | 4 |
| CONT 1 | 22.8 | 17.8 | 1.1 | 1.3 |
| CONT 2 | 18.2 | 0 | 6 | 0 |
| CONT 3 | 23.3 | 29.0 | 17.9 | 0.7 |
| CONT 4 | 0 | 0 | 0 | 0 |
| CONT 5 | 23.5 | 24.4 | 19.6 | 3.9 |
| CONT 6 | 2.7 | 3.0 | 1.2 | 1.7 |
| MEAN | 15.1 | 12.4 | 7.6 | 1.3 |
| STD | 10.9 | 13.0 | 8.9 | 1.5 |
| LIPO 1 | 1.7 | 0 | 0 | 0.6 |
| LIPO 2 | 1.3 | — | 0 | 0.5 |
| LIPO 3 | — | 0 | 0 | 0 |
| LIPO 4 | 2.7 | 0.5 | 0 | 0.2 |
| MEAN | 1.9 | 0.2 | 0 | 0.3 |
| STD | 0.7 | 0.3 | 0 | 0.3 |

Figure 5:
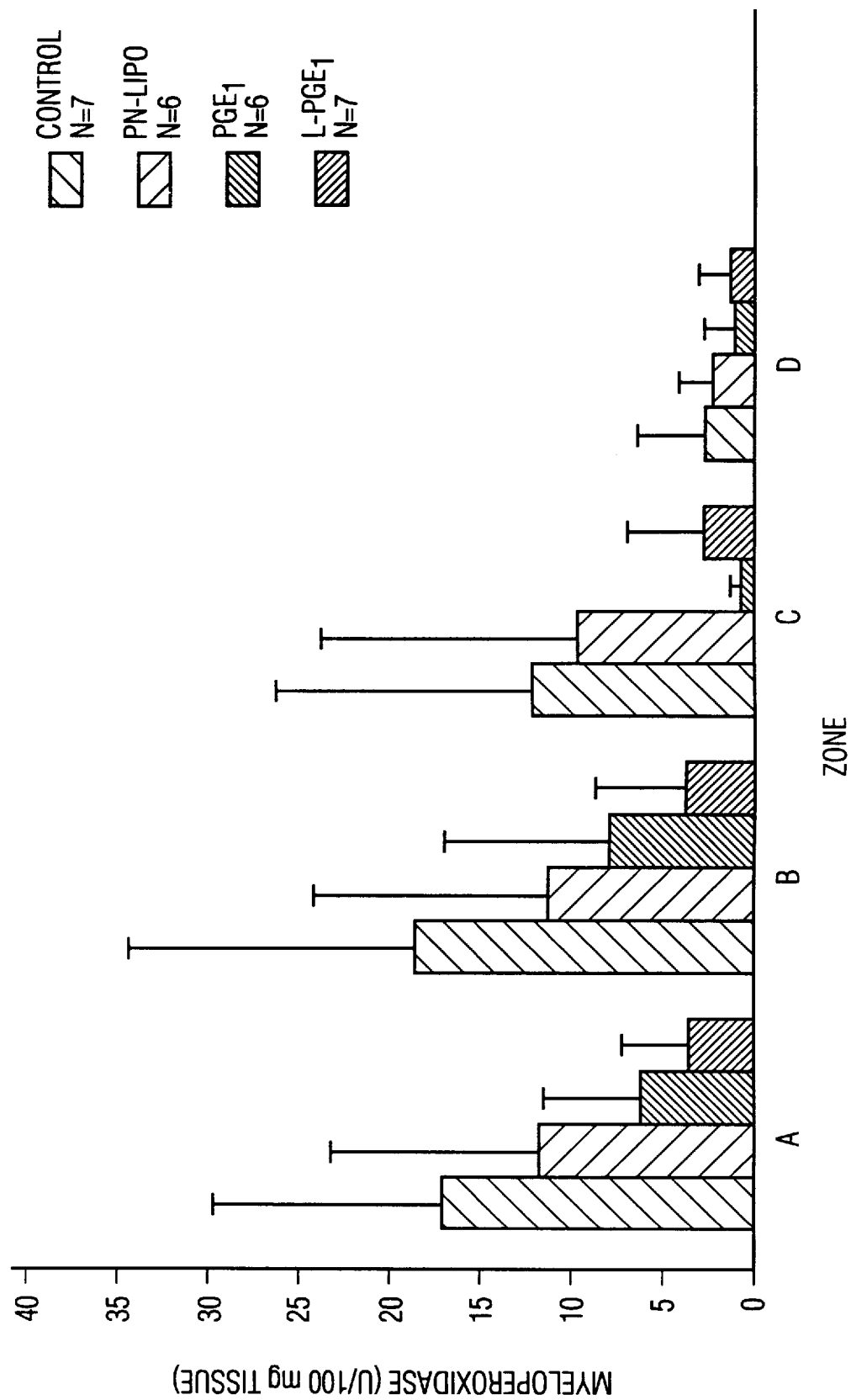
FIG. 5. Myeloperoxidase Release From Myocardial Tissue. X-axis: infarct zone, border zone, risk region, control zone (darkly shaded: control; slanted lines: empty liposomes; straight lines: free PGE1; cross-hatched: LUV-PGE1.

Additional dogs were tested in each group. FIG. 5 summarizes the results of the totality of dogs suitable for analysis in each of the four groups tested.

In the above table, a dash indicates no measurement was made for that particular value.

Example 3

In Vivo Tests for Prophylaxis of ARDS

Adult respiratory distress syndrome (ARDS) is a condition secondary to a variety of insults including, but not limited to, trauma, burns aspiration and hyperoxia. The condition is characterized by interstitial edema die to capillary injury. Once the lungs fill with fluid, breathing becomes difficult, and 5–60% of the patients die. The sequence of events leading to this catastrophic conclusion can vary depending upon the nature of the initial insult, Factors such as C3a, C5a, IL-1 and TNF activate the neutrophils, The mode of action of $PGE_1$ is independent of the mechanics of cellular activation. In the presence of $PGE_1$, neutrophils cannot be activated, and if they are already activated they will be turned off, thereby preventing the disease.

Studies were conducted on rodent models for ARDS where lung injury had been induced by either thermal injury or by direct intratracheal injection of IL-1. As noted in the following examples, doses of liposomal-$PGE_1$ prevented the leak of fluid into the lung and significantly reduced the influx of neutrophils into the lung.

Figure 6:
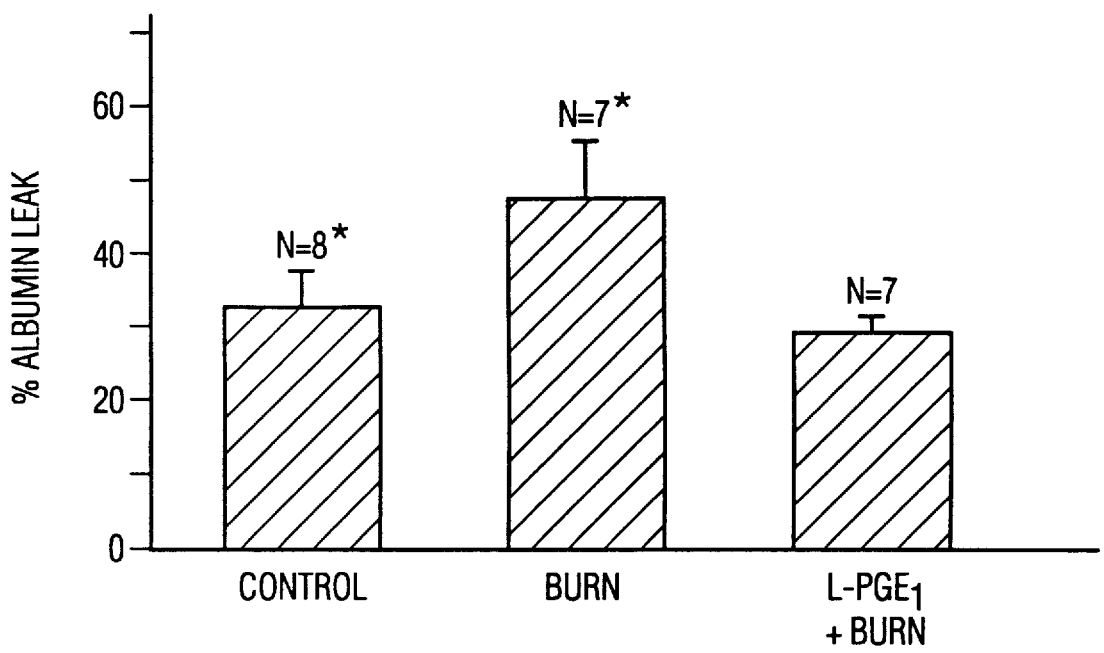
FIG. 6. Prevention of Lung Injury After Skin Thermal Injury With LUV-PGE1 Treatment. X-axis: control, burn, burn plus LUV-PGE1. Y-axis: percent albumin leak (cpm right lung/cpm blood).

The rehydrated liposomal $PGE_1$ of Example 1 was tested in vivo as a prophylactic to the onset of adult respiratory distress syndrome (ARDS). Test rats were divided into three groups containing seven or eight animals each and treated with either 8 µg/kg of liposomal $PGE_1$ or saline simultaneous with and one after thermal injury (by immersion in 70° C. water for 45 seconds). The first group was treated with liposomal $PGE_1$, the second group was not treated with the liposomal $PGE_1$, but was subjected to the same trauma and the third group was neither treated nor traumatized One hour prior to sacrifice of the rats, 125 I-albumin was injected intravenously as a marker for fluid leak into the lung. Four hours after thermal injury the animals were sacrificed. The results of the study are summarized in FIG. 6.

An effect of such traumatization is known to be the onset of ARDS, as evidenced by an increased level of albumin in the lungs of affected animals. The untreated traumatized animals all exhibited elevated levels of albumin in the lungs. Furthermore, six out of these seven test animals died. The level of albumin in the animals treated with liposomal $PGE_1$ was found to be about as low, or even lower, than the levels in the untraumatized control group. Furthermore, none of the seven $PGE_1$ treated animals died as a result of the trauma. These results show the effectiveness of liposomal $PGE_1$ as a prophylactic to the onset of ARDS.

In Vivo Tests for Treatment of ARDS Induced by Intratracheal Injection of IL-1

Figure 7:
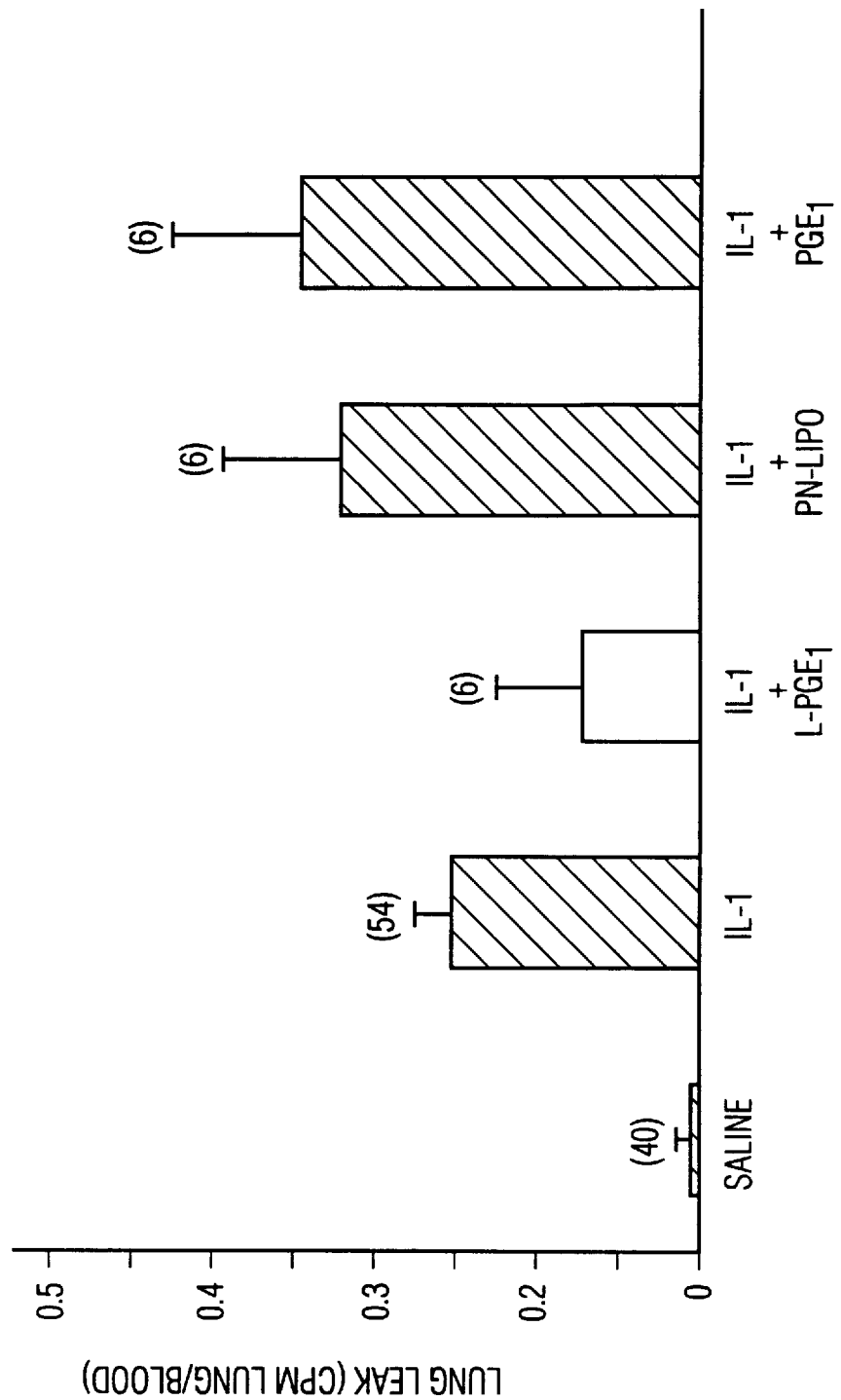
FIG. 7. Effect of Empty Liposomes or Free PGE1 on Lung Leak in Rats Given IL-1 Intratracheally. X-axis: saline control, IL-1, IL-1+LUV-PGE1, IL-1+ empty liposomes, IL-1+ free PGE1. Y-axis: lung leak (cpm lung/cpm blood).

Intratracheal instillation of recombinant IL-1 induces a neutrophil influx and lung injury in rats (FIG. 7). Liposomal $PGE_1$ treatment will decrease IL-1 induced lung injury and neutrophil influx. 50 ng of commercially available interleukin 1 (IL-1) or saline (in the control group) was instilled into the trachea of rats inducing neutrophil infiltration into the lungs and leak of fluid into the alveoli. Intravenous treatment, 6 µg/kg, of either rehydrated liposomal $PGE_1$ of Example 1, free $PGE_1$ or empty liposomes was administered 2.5 hours after IL-1 instillation in rats having received the IL-1. Of the rats analyzed 40 received only saline, 54 received IL-1 and were untreated, 6 received IL-1 and were treated with liposomal $PGE_1$, 6 received IL-1 and were treated with empty liposomes, and 6 received IL-1 and were treated with free $PGE_1$.

Four and a half hours after the IL-1 was given, after many neutrophils had already infiltrated into the tissue, the rats were injected with 125 I albumin as a marker into the bloodstream. A half an hour after the albumin was injected the animals were sacrificed, the lung removed and the leak of fluid into the lung was quantitated by determining the amount of isotope in the tissue. A lung leak index was calculated based on the count per minute (cpm) of labeled 125 I-albumin in the lung divided by the amount of labeled 125 I-albumin in the bloodstream. The lung leak is expressed on the Y-axis of FIG. 7. As noted in FIG. 7, instillation of IL-1 without treatment caused a 2.5-fold increase of lung leak above sham or animals given saline. However, when liposomal $PGE_1$ treatment was given after instillation of IL-1, the lung leak index was equal to that seen in the sham control. Importantly, treatment with neither the free $PGE_1$ nor the empty liposomes had any effect on lung leak.

This sequence of events represents that which might occur in a clinical setting. Injury was induced, and treatment was initiated at a later time after the appropriate diagnosis was made.

Example 4

Rat Endotoxemia Studies

Preparation of EPC-Containina $PGE_1$ MLVs

An egg phosphatidylcholine (EPC) stock solution (20 mg/ml in ethanol) was prepared as follows: 1 g of dried EPC was dissolved in 50 ml of absolute ethanol, with gentle swirling, in a 50-ml brown bottle with a Teflon-lined lid. The resulting solution was stored at minus 20 degrees Celsius. A $PGE_1$ stock solution (1 mg/ml in ethanol) was prepared as follows: 20 mg of dried $PGE_1$ was transferred to a 20-ml vial, to which 20 ml of absolute ethanol was added. The $PGE_1$ was dissolved in the ethanol with gentle swirling; the resulting solution was stored at minus 20 degrees Celsius.

An aliquot of the EPC stock solution (9.75 ml), and an aliquot of the $PGE_1$ stock solution (0.5 ml), were combined in a 500-ml round-bottom flask; the ethanol was removed by rotoevaporation at about 30 degrees C. for at least two hours. The dried $EPC/PGE_1$ was resuspended in a pH 4.5 buffer (e.g., 50 mM acetate, 150 mM NaCl, pH brought to 4.5 with 10N NaOH; glass beads aided in resuspension of the dried $EPC/PGE_1$) so as to form a liposome suspension. This suspension was stored at 4 degrees C.

Preparation of DPPC-Containina PGE1 MLVs

A DPPC stock solution was prepared as described above, using 1.035 g of dipalmitoyl phosphatidylcholine (DPPC) dissolved in methylene chloride. Rehydration of the dried $DPPC/PGE_1$ mixture required heating in a water bath, with swirling, at about 52 degrees C. for about 3–5 minutes.

Rat Endotoxemia Model

Fever, hypotension, changes in leukocyte counts and diarrhea are symptoms of gram-negative bacterial infections. These infections may lead to disseminated intravascular coagulation and irreversible shock. A large volume of literature indicates the involvement of leukocyte derived IL-1, IL-6 and $TNF\beta$ in mediating the progression of endotoxic shock. Because our in vitro data indicated an inhibition of these cytokines from cultured monocytes, we developed an in vivo model of rat endotoxemia, using mortality as an end point, to assess the effectiveness of $PGE_1$ and particulate formulations in attenuating LPS-induced death.

Figure 8:
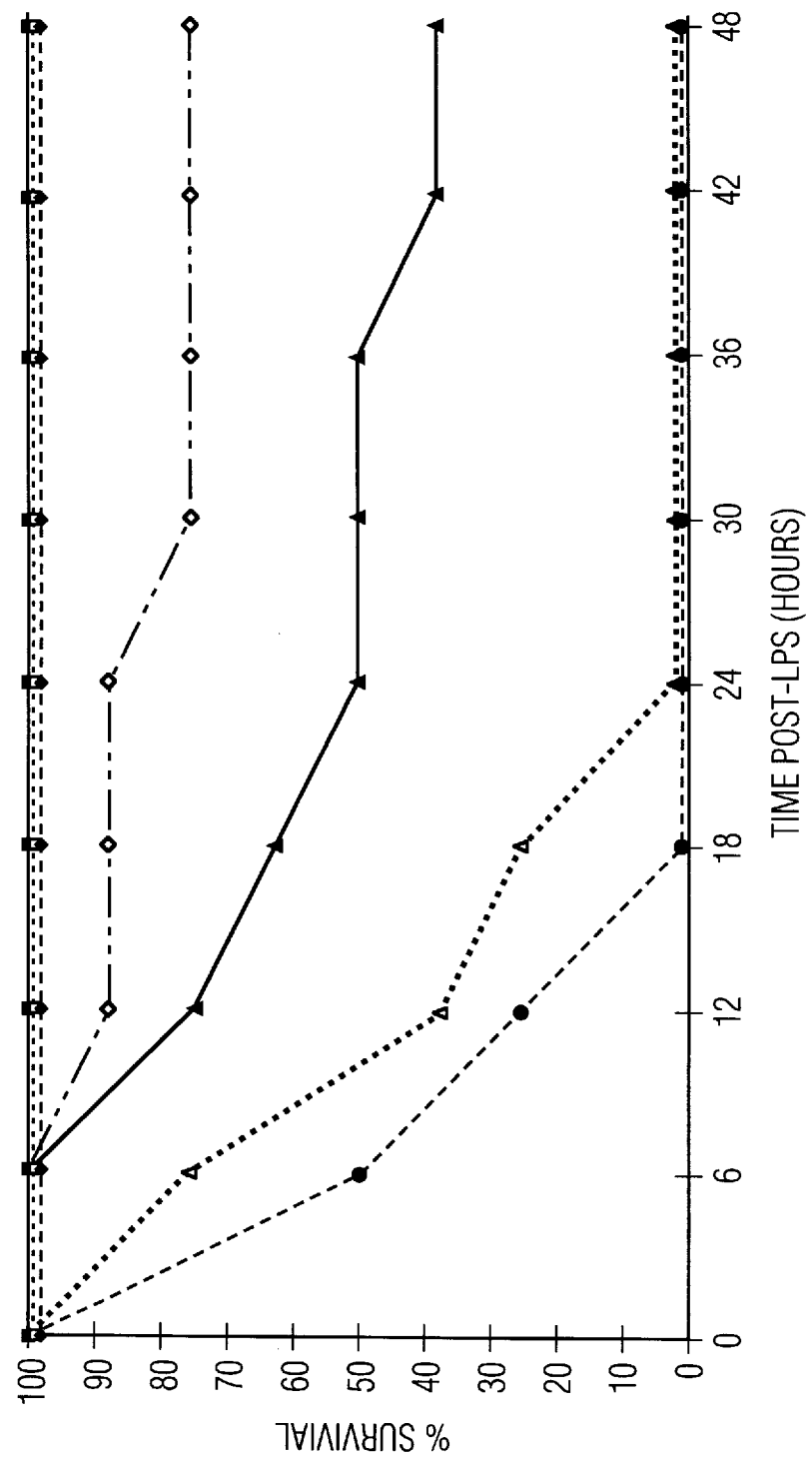
FIG. 8. Rat Endotoxemia Model. X-axis: time (days) post-LPS administration; y-axis: percent survival in treatment group. Filled squares: rats administered saline control (0 $\mu$g/kg LPS); open squares: rats administered 10 $\mu$g/kg LPS; filled diamonds: 15 $\mu$g/kg LPS; open diamonds: 25 $\mu$g/kg LPS; filled triangles: 50 $\mu$g/kg LPS; open triangles: 75 $\mu$g/kg LPS; filled circles: 100 $\mu$g/kg LPS.

Experiments were designed to establish an $LD_{50}$ for *E. coli* LPS (lipopolysaccharide; serotype 055:B5) in Sprague-Dawley rats. The data from these experiments are shown in FIG. 8, and indicate that the $LD_{50}$ is at 50 μg/kg. This LPS dosage was used in subsequent experiments, unless otherwise indicated.

Male Sprague-Dawley rats, weighing 126–150 g each, were acclimated for two days in an animal facility with food and water ad libitum. At time 0, groups of rats (n=16) were injected i.v. with either *E. Coli* lipopolysaccharide as a single bolus, or with a saline (no LPS) control. Mortality was assessed at various times (days) post-LPS administration.

Figure 9:
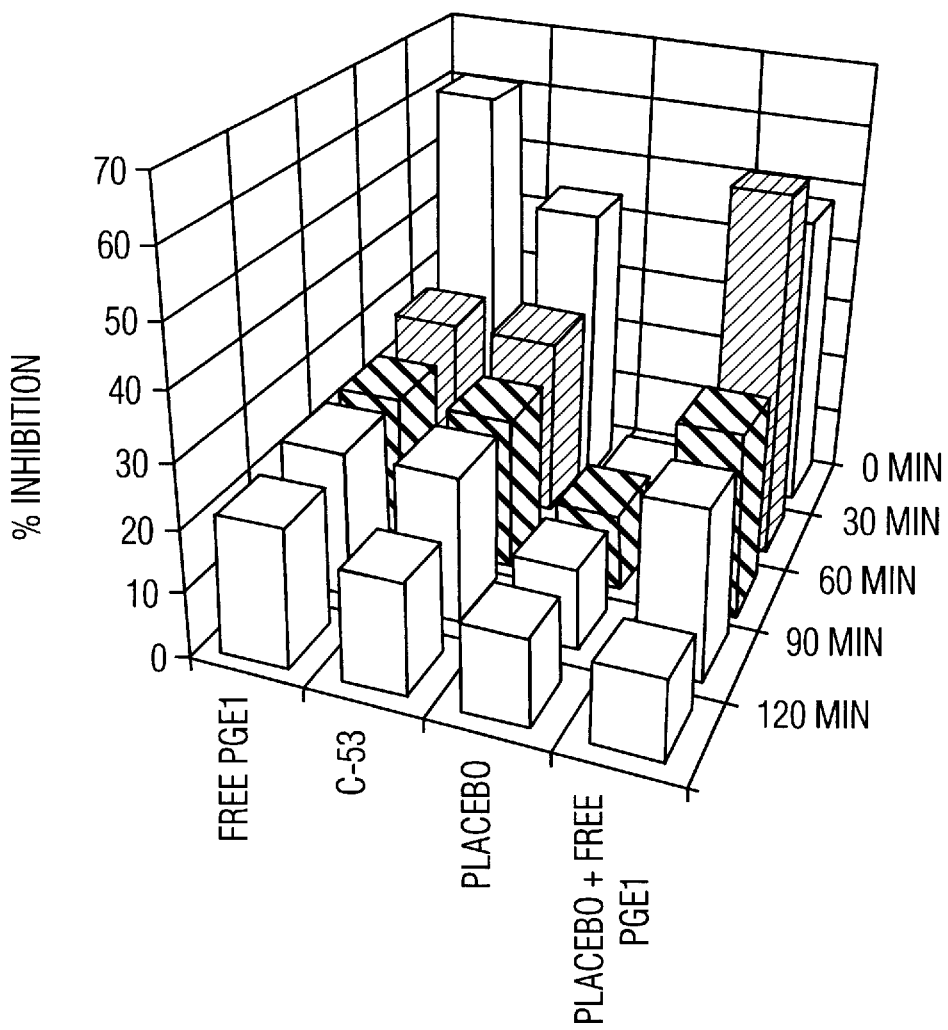
FIG. 9. Inhibition of Secretion of Human Monocyte TNF$\alpha$ and IL-1$\beta$ in Response to Lipopolysaccharide (LPS). X-axis: free PGE$_1$, LUV-PGE$_1$ (unilamellar liposomes containing PGE1 and prepared in accordance with the procedures described in Example 1), placebo LUVs (large unilamellar liposomes not containing PGE1), placebo LUVs plus free PGE$_1$; y-axis: percent inhibition of TNF$\alpha$ and IL-1$\beta$ secretion; unshaded: TNF$\alpha$; shaded: IL-1$\beta$.

Inhibition of Tumor Necrosis Factor Alpha (TNFα) and Interleukin-1 Beta (IL-1) Synthesis in Response to Lipopolysaccharide (LPS) and $PGE_1$ Adherent human monocytes were stimulated with LPS (1 μg/ml/$10^6$ cells) at time 0. Free $PGE_1$ (not entrapped in liposomes), LUV-$PGE_1$ (large unilamellar liposomes (LUVs) prepared in accordance with the procedures described in this Example), LUV-$PGE_1$ "placebo" liposomes (LUVs not containing $PGE_1$), LUV placebo liposomes plus free $PGE_1$, placebo liposomes or a saline control (no $PGE_1$) were injected simultaneously (10 μM $PGE_1$). Secreted TNFα and IL-1β were assayed at three hours. Results from these experiments are presented in FIG. 9. αβ

Attenuation of LPS-lnduced Mortality

Figure 10:
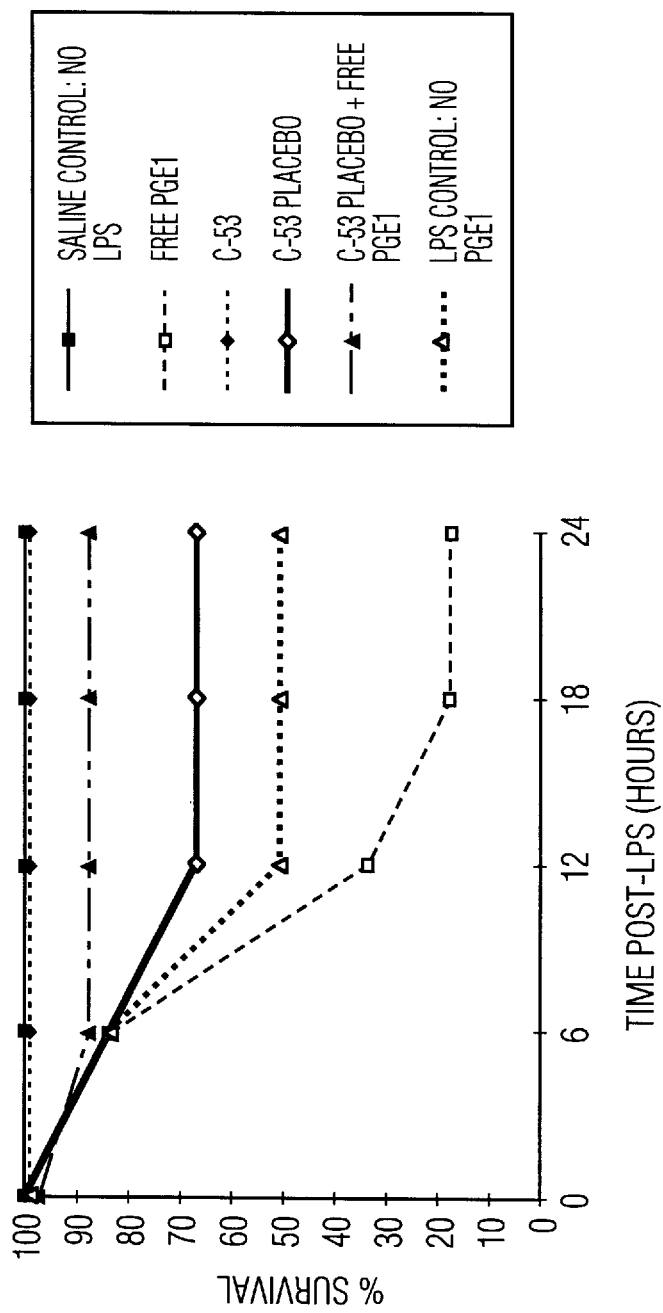
FIG. 10. Attenuation of LPS-lnduced Mortality. X-axis: time (days) post-LPS administration; y-axis: percent survival in treatment group. Filled squares: saline control (no LPS administered); filled diamonds: LUV-PGE$_1$; open diamonds: placebo LUVs plus free PGE$_1$; filled triangle: placebo LUVs; open triangles: LPS control (no liposomes or PGE$_1$); open squares: free PGE$_1$.

Male Sprague-Dawley rats were injected i.v. with 50 μg LPS/kg of body weight at time 0. Free $PGE_1$, LUV-$PGE_1$ (40 μg/kg $PGE_1$), placebo LUVs (LUVs not containing $PGE_1$; equivalent particle number to the number of liposomes given with the 40 μg/kg $PGE_1$—LUV-$PGE_1$ dose) or placebo LUVs (40 μg/kg lipid equivalency) plus free $PGE_1$ (40 μg/kg). There were 12 rats were in each treatment group. Survival was assessed in each group at 6, 12, 18 and 24 days post-LPS administration. Results are presented in FIG. 10.

Elimination of Free $PGE_1$—lnduced Mortality

Figure 11:
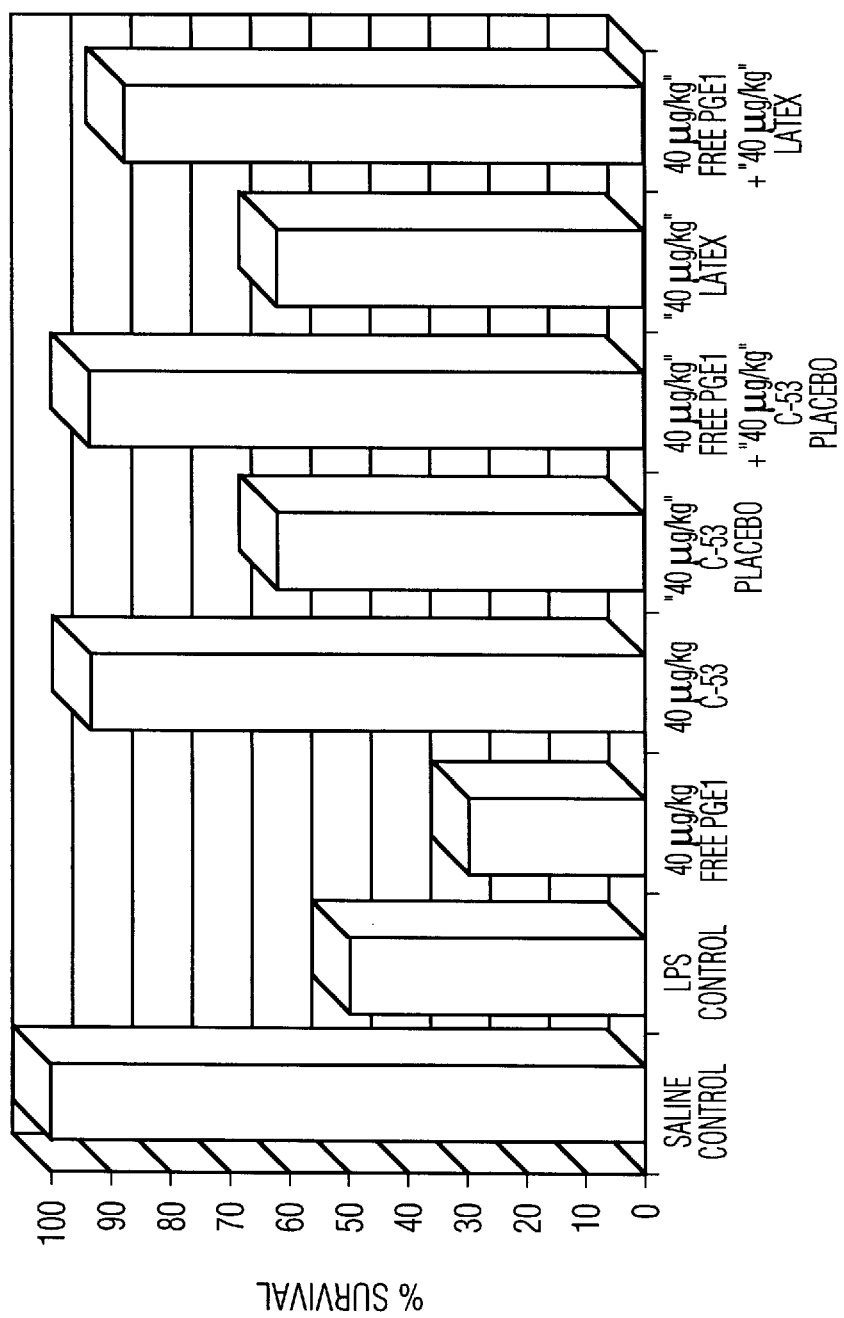
FIG. 11. Elimination of Free PGE$_1$-Induced Mortality. X-axis: Saline control (no LPS, PGE$_1$ or liposomes), LPS control (LPS, but no liposomes or PGE$_1$), LUV-PGE$_1$, placebo LUVs plus free PGE$_1$, LATEX microspheres plus free PGE$_1$, placebo LUVs, LATEX microspheres; y-axis: percent survival in treatment group.

Male Sprague-Dawley rats were injected i.v. with 50 μg/kg LPS at time 0. Free $PGE_1$ (40μg/kg), LUV-$PGE_1$ (40 μg/kg $PGE_1$), placebo LUVs (40 μg/kg lipid equivalency, i.e., the number of placebo LUVs was equal to the number of LUVs present in connection with a dose of 40 micrograms of prostaglandin E1 per kg of body weight), latex microspheres (the number equivalent to the number of placebo LUVs) or latex microspheres plus free $PGE_1$ simultaneously injected i.v. Survival in treatment group (16 rats) was asset 24 hours. Results are presented FIG. 11.

What is claimed is:

1. A method of treating an animal afflicted with a cell activation/adhesion, inflammatory or toxemic disorder which comprises administering to the animal a therapeutically effective dose of a composition comprising:
 (a) a pharmaceutically acceptable carrier; and,
 (b) a unilamellar liposome comprising:
  (i) a phospholipid; and,
  (ii) a prostaglandin, wherein:
   the disorder is selected from the group consisting of reperfusion injury, systemic inflammatory response syndrome, myocardial infarction, adult respiratory distress syndrome, vasculitis, burn injury, post-traumatic shock, vaso-occlusive disorders, arthritic disorders and autoimmune disorders; and,
   between about $10^{-12}$ to about $10^{-3}$ g of the prostaglandin per kg of animal body weight is administered to the animal per therapeutically effective dose of the composition.

2. The method of claim 1, wherein the unilamellar liposome has a diameter of about 100 to 200 nm.

3. The method of claim 1, wherein the phospholipid is egg phosphatidylcholine.

4. The method of claim 1, wherein the arachidonic acid metabolite is a prostaglandin.

5. The method of claim 1, wherein the prostaglandin is an E series prostaglandin.

6. The method of claim 5, wherein the prostaglandin is prostaglandin E1.

7. The method of claim 1, wherein the disorder is adult respiratory distress syndrome.

8. The method of claim 1, wherein the disorder is acute myocardial infarction.

9. The method of claim 1, wherein between about $10^{-8}$ to $10^{-4}$ g of the metabolite per kg body weight is administered per dose.

10. The method of claim 1, wherein the disorder is adult respiratory distress syndrome or acute myocardial infarction, wherein the liposome has a diameter of about 100 to 200 nm and comprises egg phosphatidylcholine and prostaglandin E1, and wherein between about $10^{-8}$ to $10^{-4}$ g of the prostaglandin E1 per kg body weight is administered per dose of the composition.

* * * * *